(12) United States Patent
Ames

(10) Patent No.: US 7,030,154 B2
(45) Date of Patent: Apr. 18, 2006

(54) STABILITY OF LIPOIC ACID

(75) Inventor: Bruce N. Ames, Berkeley, CA (US)

(73) Assignee: Juvenon, Inc., Orinda, CA (US)

( * ) Notice: Subject to any disclaimer, the term of this patent is extended or adjusted under 35 U.S.C. 154(b) by 18 days.

(21) Appl. No.: 10/455,192

(22) Filed: Jun. 5, 2003

(65) Prior Publication Data

US 2004/0044046 A1 Mar. 4, 2004

Related U.S. Application Data

(60) Provisional application No. 60/387,125, filed on Jun. 7, 2002.

(51) Int. Cl.
*A61K 31/385* (2006.01)

(52) U.S. Cl. .................. 514/440; 514/557; 549/39; 562/507

(58) Field of Classification Search ........... 514/440, 514/557; 549/39; 562/507
See application file for complete search history.

(56) References Cited

U.S. PATENT DOCUMENTS

| | | |
|---|---|---|
| 2,840,505 A | 6/1958 | Grunert et al. |
| 2,933,430 A | 4/1960 | Rosenberg et al. |
| 3,049,549 A | 8/1962 | Reed et al. |
| 4,772,727 A | 9/1988 | Sutherland et al. |
| 5,118,505 A | 6/1992 | Koltringer |
| 5,281,722 A | 1/1994 | Blaschke et al. |
| 5,292,538 A | 3/1994 | Paul et al. |
| 5,334,612 A | 8/1994 | Kalden et al. |
| 5,569,670 A | 10/1996 | Weischer et al. |
| 5,916,912 A | 6/1999 | Ames et al. |
| 6,090,842 A | 7/2000 | Packer et al. |
| 6,136,339 A | 10/2000 | Gardiner |
| 6,191,162 B1 | 2/2001 | Byrd et al. |
| 6,197,340 B1 | 3/2001 | Byrd et al. |
| 6,235,772 B1 | 5/2001 | Packer et al. |
| 6,251,935 B1 | 6/2001 | Schoenen et al. |
| 6,288,106 B1 | 9/2001 | Pearson et al. |
| 6,335,361 B1 | 1/2002 | Hamilton |
| 2001/0043983 A1 | 11/2001 | Hamilton |

*Primary Examiner*—Amelia A. Owens
(74) *Attorney, Agent, or Firm*—Quarles Brady Streich Lang LLP; Barbara J. Luther

(57) ABSTRACT

A method of stabilizing R-α-lipoic acid includes combining R-α-lipoic acid with nicotinamide in a weight ratio between about 10:4 to about 10:8. A composition for treating oxidative stress includes R-α-lipoic acid and nicotinamide in a weight ratio of between about 10:4 and about 10:8.

6 Claims, 1 Drawing Sheet

STABILITY OF LIPOIC ACID

CROSS REFERENCE TO RELATED APPLICATION

This application claims the benefit of U.S. Provisional application 60/387,125, filed Jun. 7, 2002, which is hereby incorporated by reference.

BACKGROUND

1. Technical Field

This invention relates to the coenzyme lipoic acid and more particularly to a method of stabilizing lipoic acid with nicotinamide.

2. Description of Related Art

One of the strongest naturally occurring antioxidants is lipoic acid (LA). α-Lipoic acid is also known as thioctic acid, 1,2-dithiolane-3-pentanoic acid, 1,2-dithiolane-3-valeric acid and 6,8-thioctic acid. α-LA has a chiral carbon atom and occurs in two enantiomeric forms (R- and S-). The form of LA sold in stores is α-lipoic acid, a synthetic mixture of the natural isomer (R-) and the unnatural isomer (S-). The natural form of R-LA is not as stable as the synthetic mixture. One manufacturer, Asta Medica, sells R-LA for diabetes and has made a stable form of R-LA by crystallizing it with Tris buffer, a commonly used synthetic, but unnatural, buffer.

Biologically, LA exists as lipoamide in at least five proteins where it is covalently linked to a lysyl residue. Four of these proteins are α-ketoacid dehydrogenase complexes, the pyruvate dehydrogenase complex, the branched chain keto-acid dehydrogenase complex and the α-ketoglutarate dehydrogenase complex. Three lipoamide-containing proteins are present in the E2 enzyme dihydrolipoyl acyltransferase, which is different in each of the complexes and specific for the substrate of the complex. One lipoyl residue is found in protein X, which is the same in each complex. The fifth lipoamide residue is present in the glycine cleavage system.

Recently LA has been detected in the form of lipoyllysine in various natural sources. In the plant material studied, lipoyllysine content was highest in spinach (3.15 µg/g dry weight; 92.51 µg/mg protein). When expressed as weight per dry weight of lyophilized vegetables, the abundance of naturally existing lipoate in spinach was over three- and five-fold higher than that in broccoli and tomatoes, respectively. Lower concentrations of lipoyllysine were also detected in garden pea, Brussels sprouts and rice bran. Lipoyllysine concentration was below detection limits in acetone powders of banana, orange peel, soybean and horseradish, however.

In animal tissues, the abundance of lipoyllysine in bovine acetone powders can be represented in the following order: kidney>heart>liver>spleen>brain>pancreas>lung. The concentrations of lipoyllysine in bovine kidney and heart were 2.64±1.23 and 1.51±0.75 µg/g dry weight, respectively.

LA in its reduced form as dihydrolipoate (DHLA) possesses two —SH groups which provide a very low oxidation potential to the molecule (−0.29 V). Thus, LA and the DHLA redox together are excellent antioxidants capable of interacting with most forms of reactive oxygen species, recycling other antioxidants and additionally reducing oxidized disulfide groups in biological systems. These molecules then may recuperate their biological reducing power and function. These qualities of LA and DHLA make it also one of the most important molecules in redox signaling. A good example of this is the ability of this metabolically active pair to increase glucose uptake in an insulin-mimic effect.

Various enantiomeric forms of α-LA, and combinations and derivatives thereof (including its reduced form), have been used to treat numerous conditions. For example, U.S. Pat. Nos. 5,650,429 and 5,532,269 disclose the use of LAs in the treatment of circulatory disorders. U.S. Pat. No. 5,569,670 discloses combinations of LAs and vitamins in compositions useful for producing analgesic, anti-inflammatory, antinecrotic, anti-diabetic and other therapeutic effects. U.S. Pat. No. 5,334,612 describes certain alkylated derivatives of LA and their use in treatment of retroviral diseases. U.S. Pat. No. 5,084,481 discloses the use of reduced LA (DHLA) and salts thereof in treating inflammatory diseases. U.S. Pat. No. 6,693,664 discloses use of LA and DHLA in the treatment of diabetes. U.S. Pat. No. 5,508,275 discloses a variety of lipid-selective antioxidants, including lipoic acid derivatives.

LA suffers from certain disadvantages, however. In particular, the natural form R-LA is unstable above 40° C., so it can degrade under some warehousing conditions. Also LA is hygroscopic. What is needed is stabilization of this natural form of LA with a natural salt.

SUMMARY OF THE INVENTION

It is an object of this invention to provide a more stable formulation of LA and to make LA readily usable by the body.

A method of stabilizing R-α-lipoic acid includes combining R-α-lipoic acid with nicotinamide in a weight ratio between about 10:4 to about 10:8, preferably between about 10:5 to about 10:7, and most preferably 10:6. A composition for treating oxidative stress includes R-α-lipoic acid and nicotinamide in a weight ratio of between about 10:4 and about 10:8, preferably between about 10:5 to about 10:7, and most preferably about 10:6.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION

Figure 1:
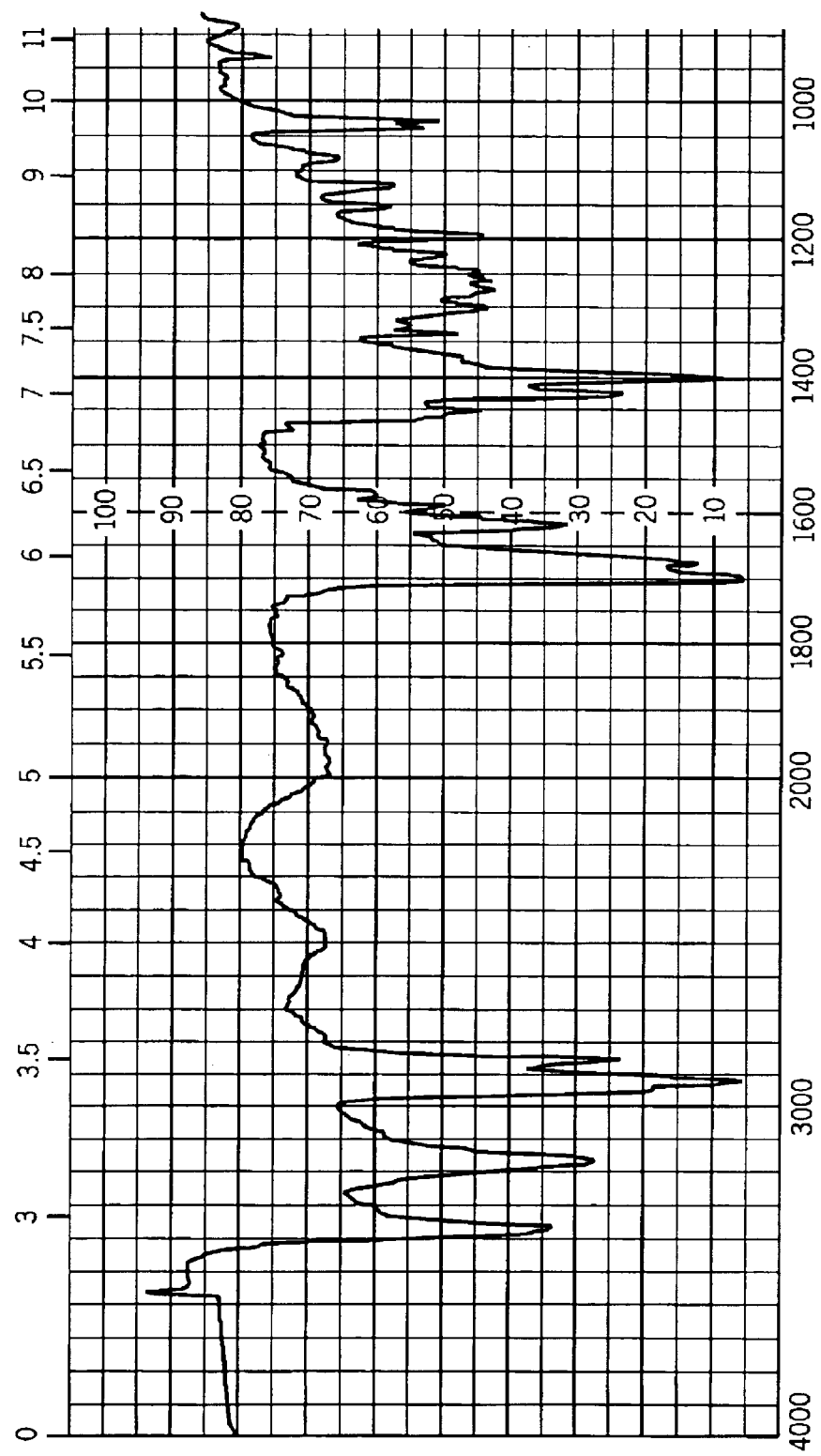
FIG. 1 is an infrared spectra of nicotinamide-a-lipoate crystals as mineral oil mulls spread on sodium chloride-polished crystal plates.

Those of ordinary skill in the art will realize that the following description of the present invention is illustrative only and not in any way limiting. Other embodiments of the invention will readily suggest themselves to such skilled persons.

The present invention is a method of stabilizing R-LA. The method comprises the crystallization of R-LA with nicotinamide. Nicotinamide is a natural form of the vitamin niacin and thus, provides a stable crystalline form of R-LA that is all natural. The amount of nicotinamide at non-toxic doses is about 20 milligrams (mg) to about 100 mg.

The resulting product can be utilized alone, or in combination with vitamin supplements, food products, and the like.

Pharmaceutical compositions including the inventive combinations are also provided. The preparation of the pharmaceutical compositions of the invention is carried out in a known manner.

Useful carriers and auxiliaries for the inventive combinations include gelatin, natural sugars such as raw sugar or lactose, lecithin, pectin, starches (e.g., corn starch or amylose), cyclodextrins and cyclodextrin derivatives, dextran, polyvinyl pyrrolidone, polyvinyl acetate, gum arabic, alginic acid, xylose, talcum, lycopodium, silica gel (e.g., colloidal silica gel), cellulose, cellulose derivatives such as cellulose ethers (e.g., HPMC), $C_{12-22}$ fatty acids and magnesium, calcium or aluminum salts thereof (e.g., stearates), emulsifiers, oils and fats, in particular vegetable (e.g., peanut oil, castor oil, olive oil, sesame oil, cottonseed oil, corn oil, wheat germ oil, sunflower seed oil, cod liver oil), glycerol esters and partial or complete polyglycerol esters of saturated fatty acids, pharmaceutically acceptably mono- or multivalent alcohols and polyglycols (e.g., polyethylene glycol and derivatives thereof), esters of $C_{2-22}$ aliphatic saturated or unsaturated fatty acids (preferably $C_{10-18}$ acids) with monovalent $C_{1-20}$ aliphatic alcohols or multivalent alcohols such as glycols, glycerol, diethylene glycol, pentaerythritol, sorbitol, mannitol and the like (which may optionally also be etherified), esters of citric acid with primary alcohols, acetic acid, urea, benzyl benzoate, dioxolanes, glyceroformals, tetrahydrofurfuryl alcohol, polyglycol ethers with $C_{1-12}$ alcohols, dimethylacetamide, lactamides, lactates, ethylcarbonales, silicones (e.g., medium-viscosity polydimethyl siloxanes), calcium carbonate, sodium carbonate, calcium phosphate, sodium phosphate, magnesium carbonate, etc.

Additional useful additives include disintegrants, such as cross-linked polyvinyl pyrrolidone, sodium carboxymethyl starch, sodium carboxymethyl cellulose or microcrystalline cellulose.

The inventive combinations can be coated with conventional coating materials such as polymers and copolymers of acrylic acid and/or methacrylic acid and/or their esters (e.g., Eudragit® copolymers), polyvinyl acetate, fats, oils, waxes, fatty alcohols, hydroxypropyl methyl cellulose phthalate or -acetate succinate, cellulose acetate phthalate, starch acetate phthalate, polyvinyl acetate phthalate, carboxy methyl cellulose, methyl cellulose phthalate, methyl cellulose succinate, zein, ethyl cellulose, ethyl cellulose succinate, shellac, gluten, ethylcarboxyethyl cellulose, ethacrylate-maleic acid anhydride copolymer, maleic acid anhydride-vinyl methyl ether copolymer, styrol-maleic acid copolymer, 2-ethyl-hexyl-acrylate maleic acid anhydride, crotonic acid-vinyl acetate copolymer, glutaminic acid/glutamic acid ester copolymer, carboxymethylethyl-cellulose glycerol monooctanoate, cellulose acetate succinate, and polyarginin.

Useful plasticizing agents that can be used as coating materials include citric and tartaric acid esters (acetyltriethyl citrate, acetyl tributyl-, tributyl-, triethyl-citrate), glycerol and glycerol esters (glycerol diacetate, -triacetate, acetylated monoglycerides, castor oil), phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate, benzophenone; diethyl- and dibutylsebacate, dibutylsuccinate, dibutyltartrate, diethylene glycol dipropionate, ethyleneglycol diacetate, -dibutyrate, -dipropionate, tributyl phosphate, tributyrin, polyethylene glycol sorbitan monooleate (polysorbates such as Polysorbate 80), and sorbitan monooleate.

Then the inventive combinations are solutions or suspensions, it is useful to employ solvents such as water or physiologically acceptable organic solvents including alcohols such as ethanol, propanol, isopropanol, 1,2-propylene glycol, polyglycols and their derivatives, fatty alcohols, partial esters of glycerol, oils such as peanut oil, olive oil, sesame oil, almond oil, sunflower oil, soya bean oil, castor oil, bovine hoof oil, paraffins, dimethyl sulphoxide, triglycerides and the like.

Injectable solutions or suspensions including the inventive combinations can be prepared using non-toxic parenterally acceptable diluting agents or solvents, such as water, 1,3-butanediol, ethanol, 1,2-propylene glycol, polyglycols mixed with water, glycerol, Ringer's solution, isotonic salt solution or also hardened oils including synthetic mono- or diglycerides or fatty acids such as oleic acid.

Solubilizers and emulsifiers useful in preparing compositions according to the invention include polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols and fatty acids.

For aqueous injection and drinkable solutions, the following stabilizers and solubilizers can be advantageously employed: $C_{2-4}$ aliphatic mono- and multivalent alcohols such as ethanol, n-propanol and glycerol, polyethylene glycols with molecular weights between 200–600, diethylene glycol monoethyl ether, 1,2-propylene glycol, organic amides (e.g., amides of aliphatic $C_{1-6}$ carboxylic acids with ammonia or primary, secondary or tertiary $C_{1-4}$ amines or $C_{1-4}$ hydroxy amines such as urea, urethane, acetamide, N-methyl acetamide, N,N-diethyl acetamide, N,N-dimethyl acetamide, $C_{2-6}$ aliphatic amines and diamines such as ethylene diamine, hydroxyethyl theophylline, tromethamine (e.g., as 0.1 to 20% aqueous solution), and aliphatic amino acids.

Preservatives, stabilizers, buffer substances, flavor correcting agents, sweeteners, colorants and antioxidants can also be employed. Antioxidants can be employed as preservatives, but at higher concentrations antioxidants may serve as co-active ingredients with the inventive combinations (i.e., synergistic activity may occur).

Useful antioxidants include sodium sulphite, sodium hydrogen sulphite, sodium metabisulphite, selenium, inorganic and organic selenium compounds and salts such as sodium selenite, ascorbic acid, ascorbyl palmitate, myristate and stearate, gallic acid, gallic acid alkyl ester, butylhydroxyanisol, nordihydroguaiacic acid and tocopherols, as well as synergists (substances which bind heavy metals through complex formation, for example lecithin, ascorbic acid, phosphoric acid ethylene, diamine tetraacetic acid, citrates, and tartrates). Compositions including selenium salts such as sodium selenite may be beneficial.

Preservatives useful in the inventive compositions include, for example, sorbic acid, p-hydroxybenzoic acid esters, benzoic acid, sodium benzoate, trichloroisobutyl alcohol, phenol, cresol, benzethonium chloride, chlorhexidine and formalin derivatives.

The pharmaceutical compositions may be applied to the skin or mucous membranes or to the inside of the body. Application methods include but are not limited to, oral, enteral, pulmonal, nasal, lingual, intravenous, intra-arterial, intracardial, intramuscular, intraperitoneal, intracutaneous, subcutaneous and transdermal.

The inventive compositions can also be formulated as cosmetic preparations, such as lotions, sun screens, ointments, solutions, creams, liposomes and emulsions. Conventional cosmetic additives, carriers, etc. can be combined with the inventive compositions to produce the desired cosmetic preparations in accordance with methods known to those skilled in the art.

Tablet and capsule compositions of the invention advantageously include up to about 1000 mg of R-LA and about 600 mg of nicotinamide. Emulsions and liposomes advantageously include up to about 10% (w/v) of R-LA and 6% of nicotinamide. Micellar solutions beneficially contain up to about 20 wt % (w/v) of R-LA and 12% of nicotinamide.

The exact dosage used will vary depending on the particular compound of the invention selected, the age, size, and health of the subject, and the nature and severity of the condition to be treated. However, the appropriate dosage may be determined by one of ordinary skill by routine experimentation, following the guidance set forth herein. As a general guideline, a compound of the invention may be administered daily in a dose of one or two tablets (see below) as a dietary supplement for aiding mitochondrial metabolism.

Suitable subjects include, without limitation, mammals, such as humans, horses, cattle, swine, dogs, cats, and the like, and cells in culture, including mammalian cells, yeast, bacterial cells and the like.

The present invention is illustrated by the following non-limiting example.

EXAMPLE 1

A solution of 3.3 g of (R)-(+)-α-lipoic acid in 20 mL methanol was added to a solution of 2.0 g nicotinamide (Sigma) in 20 mL methanol. The mixture was stripped of solvent on the rotary evaporator to yield an off-white solid. This was triturated under 25 mL of anhydrous ether, stirred well and separated by filtration. There was obtained 3.1 g of a pale yellow crystalline powder.

A small quantity of the powder as a mineral oil mull spread was spread on NaCl polished crystal plates. The plate was placed in a Beckman Infrared Spectrophotometer Accu-Lab 2 grating machine, linear in wave number. The results are shown in FIG. 1. Spectrophotometry was repeated at about 3 and 17 months and was essentially the same, indicating essentially no change in either the crystal form or chemical composition of this salt on standing under ambient conditions (light and temperature) for over a year.

EXAMPLE 2

Serving Size: 1 Tablet

Servings Per Container: 60

| Content of tablet | Amount Per Serving | % Daily Value |
|---|---|---|
| Sodium | 3 mg | <1 |
| Nicotinamide | 59 mg | 300 |
| R-α-Lipoic Acid | 100 mg | * |
| Acetyl-L-Carnitine HCl | 500 mg | * |

*Daily Value not established.

Ingredients include stearic acid, silicon dioxide, croscarmellose sodium, acacia, magnesium stearate and a white cellulose film coat containing titanium dioxide.

What is claimed is:

1. A method of stabilizing R-α-lipoic acid, the method comprising combining R-α-lipoic acid with nicotinamide in a weight ratio between about 10:4 to about 10:8.

2. The method of claim 1 wherein the weight ratio is between about 10:5 and about 10:7.

3. The method of claim 1 wherein the weight ratio is about 10:6.

4. A composition for treating oxidative stress comprising R-α-lipoic acid and nicotinamide in a weight ratio of between about 10:4 and about 10:8.

5. The composition of claim 4 wherein the weight ratio is between about 10:5 and about 10:7.

6. The composition of claim 4 wherein the weight ratio is about 10:6.

* * * * *